United States Patent [19]

Walsh et al.

[11] Patent Number: 4,960,776
[45] Date of Patent: Oct. 2, 1990

[54] 4-ARYL-N-(ALKYLAMINOALKYL, HETEROCYCLICAMINO AND HETEROCYCLICAMINO)ALKYL)-1-PIPERAZINECARBOXAMIDES

[75] Inventors: David A. Walsh, Richmond; Albert D. Cale, Jr., Mechanicsville, both of Va.

[73] Assignee: A. H. Robins Company, Inc., Richmond, Va.

[21] Appl. No.: 7,592

[22] Filed: Jan. 28, 1987

[51] Int. Cl.⁵ ............... A61K 31/495; A61K 31/445; C07D 401/12; C07D 403/12
[52] U.S. Cl. .................. 514/252; 514/210; 514/212; 514/235.8; 514/255; 540/598; 544/121; 544/357; 544/359; 544/360; 544/366
[58] Field of Search ............ 540/598; 544/359, 360, 544/366, 390, 121, 357; 514/210, 212, 252, 255, 234, 235.8

[56] References Cited

U.S. PATENT DOCUMENTS

| | | | |
|---|---|---|---|
| 2,642,255 | 10/1949 | Morren | 544/390 |
| 4,308,387 | 12/1981 | Björk | 544/390 |
| 4,446,133 | 5/1984 | Okazaki et al. | 544/390 |
| 4,593,102 | 6/1986 | Shanklin, Jr. | 546/193 |
| 4,594,343 | 6/1986 | Shanklin, Jr. et al. | 514/330 |
| 4,670,456 | 6/1987 | Weber et al. | 514/252 |

OTHER PUBLICATIONS

Ried et al., CA 93-114295a.

Primary Examiner—Cecilia Shen

[57] ABSTRACT

Novel 4-aryl-N-[2-(dialkylamino and heterocyclicamino)alkyl]-1-piperazinecarboxamides of the formula:

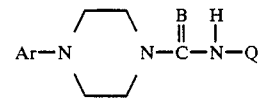

wherein B is oxygen or sulfur; Ar is selected from

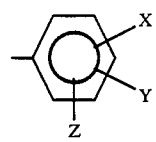

or 2, 3 or 4-pyridyl; X is selected from hydrogen, halogen, loweralkyl, loweralkoxy, amino, dimethylamino, nitro, trifluoromethyl, cyano, acetyl, acetylamino, aminocarbonyl, carboxy or loweralkylcarboxylic acid ester; Y is selected from hydrogen, halogen, loweralkyl, loweralkoxy, nitro, trifluoromethyl, cyano, acetylamino, aminocarbonyl, carboxy or loweralkyl carboxylic acid ester; Z is selected from hydrogen, loweralkyl or loweralkoxy; Q is selected from

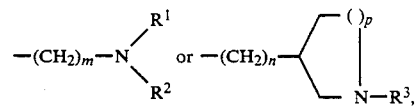

m is 1 to 3 inclusive; n is zero or 1; p is zero to 3 inclusive; $R^1$, $R^2$ and $R^3$ are loweralkyl and may be the same or different, or $R^1$ and $R^2$ taken together with the adjacent nitrogen atom may be form a heterocyclic residue; and the pharmaceutically acceptable salts thereof are disclosed. The compounds are useful in a method of combating allergic response associated with anaphylactic sensitivity in animals and humans.

73 Claims, No Drawings

4-ARYL-N-(ALKYLAMINOALKYL, HETEROCYCLICAMINO AND HETEROCYCLICAMINO)ALKYL)-1-PIPERAZINECARBOXAMIDES

BACKGROUND OF THE INVENTION

1. Field of Invention

This invention relates to novel 4-aryl-N-(alkylaminoalkyl, heterocyclicamino and heterocyclicamino-alkyl)-1-piperazinecarboxamides. useful in a method of combating allergic response in a living animal body in need thereof and pharmaceutical compositions therefor. The method employs the compounds in inhibiting Type I allergic response (Gell and Coombs Classification of Immune Responses). The compounds prevent release of histamine as well as antagonize end organ effects of mediators involved in the immediate hypertensivity response and, as such, are useful in treating allergic phenomena which includes asthma, rhinitis, atopic dermatitis, chronic hives, allergic conjunctivitis, and the like.

2. Information Disclosure Statement

Certain N-[(amino)alkyl]-1-pyrrolidine-1, piperidine and 1-bromopiperidinecarboxamides are disclosed in U.S. Pat. Nos. 4,547,514; 4,593,102; and 4,594,343. The compounds have ring-carbon substitution of aryloxy, arylthio, arylsulfinyl, arylsulfonyl or α,α-diarylacetamido and have application as antiarrhythmic agents.

OBJECTS AND SUMMARY OF THE INVENTION

The novel 4-aryl-N-(alkylaminoalky, heterocyclicamino and heterocyclicamino-alkyl)-1-piperazinecarboxamides. have the formula:

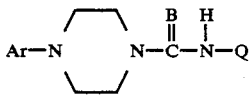

Formula I wherein;

B is oxygen or sulfur;

Ar is selected from

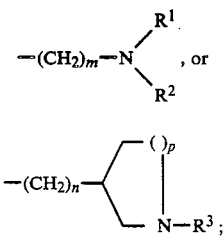

or 2, 3 or 4-pyridyl;

X is selected from hydrogen,
halogen,
loweralkyl,
loweralkoxy,
amino,
dimethylamino,
nitro,
trifluoromethyl,
cyano,
acetyl,
acetylamino,
aminocarbonyl,
carboxy, or
loweralkyl carboxylic acid ester;

Y is selected from hydrogen,
halogen,
loweralkyl,
loweralkoxy,
nitro,
trifluoromethyl,
cyano,
acetyl,
acetylamino,
aminocarbonyl,
carboxy, or
loweralkyl carboxylic acid ester;

Z is selected from
hydrogen,
loweralkyl, or
loweralkoxy;

Q is selected from

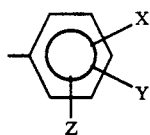

m is 1 to 3 inclusive;

n is zero or 1;

p is zero to 3 inclusive;

$R^1$, $R^2$ and $R^3$ are loweralkyl and may be the same or different, or $R^1$ and $R^2$ taken together with the adjacent nitrogen atom may form a heterocyclic residue, and the pharmaceutically acceptable salts thereof.

In the further definition of symbols in the formulas hereof and where they appear elsewhere throughout this specification and claims, the terms have the following significance.

The term "loweralkyl" as used herein includes straight and branched chain radicals of up to eight carbons inclusive and is exemplified by such group as methyl, ethyl, propyl, isopropyl, butyl, sec-butyl, tert-butyl, amyl, isoamyl, hexyl, heptyl, and octyl radicals, and the like. The term "loweralkoxy" has the formula "—O—loweralkyl."

The term "halogen" when referred to herein includes fluorine, chlorine, bromine, and iodine, preferably fluorine, chlorine and bromine.

The term "heterocyclic residue" as used herein refers to 1-azetidinyl, 1-pyrrolidinyl, 1-piperidinyl, 1-piperazinyl, 4-phenylpiperazin-1-yl, 2,6-loweralkylpiperidin-1-yl, 4-hydroxy-4-phenylpiperidin-1-yl, 4-cyano-4-phenylpiperidin-1-yl, 4-phenyl-1,2,3,6-tetrahydropyridin-1-yl, 4-loweralkylpiperazin-1-yl, (4-phenyl-loweralkyl)-piperazin-1-yl, or 4-morpholinyl radicals.

"Pharmaceutically acceptable salts" are the acid addition salts formed with any acid which is physiologically compatible in warm-blooded animals, such salts being formed by either strong or weak acids, and when Ar is substituted by carboxy, the physiologically acceptable metal salts. Representative of strong acids forming acid addition salts are hydrochloric, hydrobromic, sulfuric, and phosphoric acids. Representative of weak acids forming acid addition salts are fumaric, maleic, succinic, tartaric, oxalic, citric, hexamic, and the like. Suitable carboxylic acid salts are those formed with alkali metal hydroxides such as sodium and potassium hydroxides and carbonates, alkaline earth metal hydroxides such as calcium and magnesium. Aluminum and copper salts are also suitable carboxylate salts. Suitable quaternary salts include the loweralkyl halides and loweralkyl sulfates.

The primary screening method used to detect anti-allergy properties of the compounds of Formula I is a modification of the procedure of R. R. Martel and J. Klicius, Intern. Arch. Allergy Appl. Immunology, Vol 54, pp 205–209 (1977) which measures the effect of oral administration of the compound on the volume of a rat paw which was previously injected with anti-egg albumen serum and is described in detail under Pharmacology Methods hereinbelow.

A method of studying potency in preventing guinea pig anaphylaxis relative to known anti-allergy drugs is also described hereinbelow.

The Gell and Coombs Classification of Immune Responses referred to hereinabove is well known in the art and is described in ESSENTIAL IMMUNOLOGY 3rd Ed (1977), (Blackwell Scientific Publications) printed by William Clowes & Sons, Limited, London, Beccles & Colchester.

The general method for preparing compounds of Formula I is diagrammed in Chart I.

CHART I

Preparation of 4-aryl-N-(alkylaminoalkyl, heterocyclicamino and heterocyclicamino-alkyl)-1-piperazinecarboxamides.

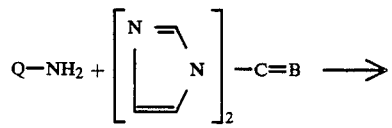

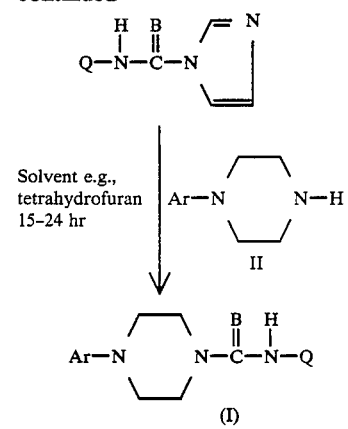

B=O or S; Q and Ar are as defined under Formula I above except Ar is not substituted by $NH_2$.

Several of the arylpiperazine reactants are available commercially and were purchased. Others were prepared by the method described by Jain, P. C. et al., in J. MED. CHEM. 10, 812–818 (1967) wherein the appropriate aniline is reacted with bis($\beta$-chloroethyl)amine hydrochloride in refluxing butanol for 24 hr, followed by cooling, adding anhydrous potassium carbonate and refluxing for another 48 hr. The reaction mixture is filtered hot, the filtrate cooled and the precipitated N-arylpiperazine hydrochlorides separated and washed with appropriate solvents. The bases are liberated by basifying solutions of the hydrochlorides. Other compounds were prepared from cyanophenyl bromide and piperazine and some modified thereafter. Still others were prepared by reacting substituted fluorobenzene and 1-benzylpiperazine and thereafter hydrogenating off the benzyl group using palladium on carbon catalyst.

Schematic equations for preparing aminophenyl and dimethylaminophenyl derivatives are given in Chart II.

CHART II

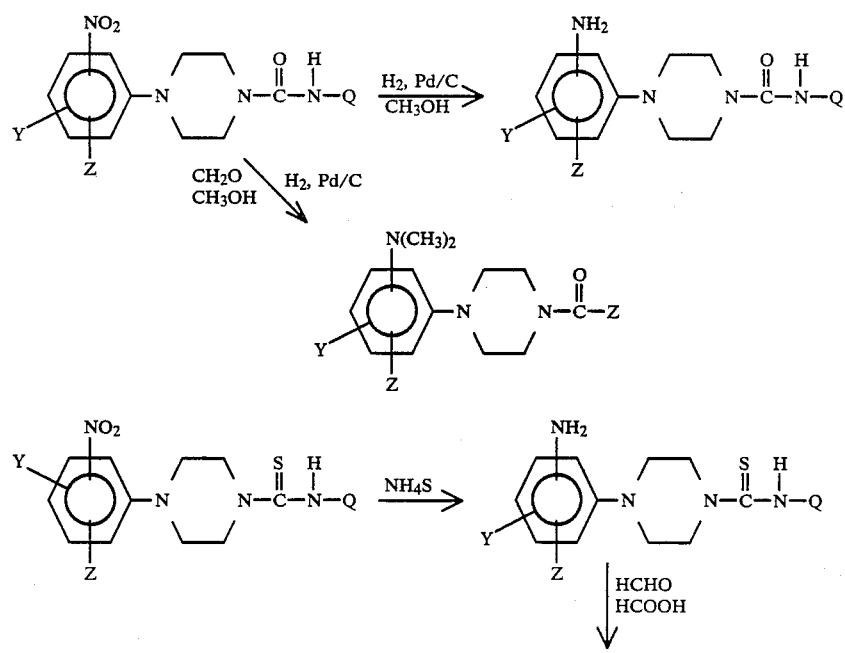

CHART II
-continued

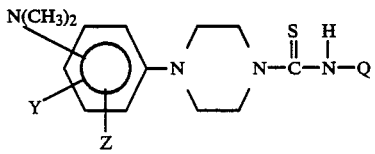

The following preparations illustrate the synthesis of certain intermediates not readily available otherwise. Preparation 11 illustrates the synthesis of novel 3-amino-1-substituted azetidines, which compounds are intended to be the subject of a separate patent application.

Preparation 1

1-(3,4,5-Trimethoxyphenyl)piperazine.

A solution of 44.3 g (0.25 mole) of bis(2-chloroethyl)amine hydrochloride and 45.5 g (0.25 mole) of 3,4,5-trimethoxyaniline in 550 ml of absolute ethanol was heated at reflux for 16 hr under a nitrogen atmosphere. The mixture was cooled and 50.0 g (0.36 mole) of potassium carbonate was added and heating was continued for 16 hr. The hot mixture was filtered, the filtrate was concentrated under reduced pressure and the residue was triturated with ethyl acetate to obtain the crude hydrochloride. The collected solid was recrystallized from 2-propanol/methanol and dissolved in 5.9 g sodium hydroxide. The solution was continuously extracted with chloroform for 5 hr. The organic layer was dried over magnesium sulfate, concentrated under reduced pressure and the residue was triturated with cyclohexane/petroleum ether (30°–60° C.) to give 23.6 g (38%) of white solid, m.p. 73°–77° C.

Analysis: Calculated for $C_{13}H_{20}N_2O_3$: C,61.89; H,7.99; N,11.10

Found: C,61.53; H,8.01; N,11.01

Preparation 2

1-(3,4-Dichlorophenyl)piperazine.

This compound was prepared according to the procedure of Preparation 1. A mixture of 44.6 g (0.25 mole) of bis(2-chloroethyl)amine hydrochloride, 40.5 g (0.25 mole) of 3,4-dichloroaniline and 50.0 g (0136 mole) of potassium carbonate in a total volume of 500 ml of n-butanol gave an oil as residue. Trituration of the oil with petroleum ether (30°–60° C.) gave 16.0 g of white solid, m.p. 62°–65° C.

Analysis: Calculated for $C_{10}H_{12}Cl_2N_2$: C,51.97; H,5.23; N,12.12

Found: C,51.75; H,5.24; N,12.01

Preparation 3

1-(4-Bromophenyl)piperazine monohydrochloride.

This compound was prepared according to the procedure of Preparation 1. A mixture of 5.4 g (0.03 mole) of bis-(2-chloroethyl)amine hydrochloride, 5.2 g (0.03 mole) of p-bromoaniline and 5.0 g (0.04 mole) of solid potassium carbonate in a total volume of 50 ml of absolute ethanol gave 2.9 g (26%) of a semisolid. A 0.5 g portion of the base was converted to the hydrochloride using ethereal hydrogen chloride which was recrystallized from methanol/ethyl ether to give white solid, m.p. 240° C. with decomposition.

Analysis: Calculated for $C_{10}H_{14}BrClN_2$: C,43.27; H,5.11; N,10.12

Found: C,43.01; H,5.08; N,10.09

Preparation 4

4-(1-Piperazinyl)benzonitrile monohydrochloride.

A mixture of 27.3 g (0.15 mole) of p-bromobenzonitrile, 38.7 g (0.45 mole) of piperazine and 42.0 g (0.30 mole) of solid potassium carbonate in a total volume of 60 ml of n-butanol was heated at reflux for 16 hr under a nitrogen atmosphere. The mixture was concentrated under reduced pressure and the slurry partitioned between 10% sodium hydroxide and chloroform. The chloroform layer was separated, dried over magnesium sulfate, and concentrated under reduced pressure to give an oil. The oil was eluted through a 400 g silica gel column with a 10% methanol in methylene chloride mixture. The appropriate fractions were concentrated under reduced pressure to give a golden oil. Trituration of this oil with ethyl acetate gave a white powder. The collected white powder was stirred for 15 min in ethereal hydrogen chloride and recrystallized from methanol-water to give 1.5 g (4.5%)* of white solid, m.p. >160° C. with decomposition.

Analysis: Calculated for $C_{11}H_{14}ClN_3$: C,59.06; H,6.31; N,18.78

Found: C,58.90; H,6.32; N,18.66 *A limited product yield was obtained due to the fact that the piperazine starting material was not anhydrous. When anhydrous piperazine was used, the yield of the reaction was 20%.

Preparation 5

4-(1-Piperazinyl)benzamide.

To 8.0 g (0.04 mole) of 4-(1-piperazinyl)benzonitrile was added, with stirring, 50.0 ml (0.87 mole) of 93% sulfuric acid over a 15 min period. The mixture was stirred overnight and the resulting suspended amide was collected by filtration, rinsed with water, and allowed to air dry. The solid was recrystallized from absolute ethanol to give 1.6 g (20%) of white solid, m.p. 240°–243° C.

Analysis: Calculated for $C_{11}H_{15}N_3O$: C,64.37; H,7.37; N,20.47

Found: C,64.20; H,7.33 N,20.34

Preparation 6

1-(4-Nitrophenyl)-4-(phenylmethyl)piperazine.

To 12.5 g (0.07 mole) of methanically stirred 1-benzylpiperazine was added 10.0 g (0.07 mole) of 4-nitrofluorobenzene. After 10 minutes the mixture solidified. The yellow solid was suspended in 50 ml of ethyl acetate and ethereal hydrogen chloride was slowly added to the stirring mixture under a nitrogen atmosphere. The solid was collected (filtration) and partitioned between 10% sodium hydroxide solution and benzene. The benzene layer was washed with ten 100 ml portions of water, dried with anhydrous magnesium sulfate and concentrated under reduced pressure to give a yellow oil. Upon cooling, the oil crystallized. The solid was recrystallized from 2-propanol/petroleum ether (60°–110° C.) to give 9.8 g (47%) of yellow solid, m.p. 115°–118° C.

Analysis: Calculated for $C_{17}H_{19}N_3O_2$: C,68.67; H,6.44; N,14.13

Found: C,68.87; H,6.43; N,14.18

Preparation 7

4-[4-(Phenylmethyl)-1-piperazinyl]benzenamine dihydrochloride.

This compound was prepared by the hydrogenation of 9.8 g (0.03 mole) of 1-(4-nitrophenyl)-4-(phenylmethyl) piperazine in 200 ml of benzene using palladium on carbon as the catalyst. The solution was filtered and the filtrate concentrated to an oil under reduced pressure. Upon cooling, the oil crystallized to a dark purple mass. The solid was triturated with petroleum ether (60°–110° C.) for 1 hr and 9.5 g (50%) of light purple product was collected by filtration. One gram of this unstable solid was converted to the hydrochloric acid salt using ethereal hydrogen chloride and recrystallized from methanol/ethyl ether to give 100 mg of light purple solid, m.p. >240° C.

Analysis: Calculated for $C_{17}H_{23}Cl_2N_3$: C,60.00; H,6.81; N,12.35

Found: C,60.09; H,6.83; N,12.33

Preparation 8

N-[4-[4-(Phenylmethyl)-1-piperazinyl]phenyl]acetamide.

To a solution of 8.5 g (0.03 mole) of the base of 4-[4-(phenylmethyl)-1-piperazinyl]benzeneamine and 16.0 g (0.16 mole) of triethylamine in 450 ml of ethyl acetate was added, dropwise, a solution of 2.5 g (0.035 mole) of acetyl chloride in 50 ml of ethyl acetate. The mixture was magnetically stirred for 3 hr and then heated at reflux for 1 hr. The excess acetyl chloride was co-distilled with benzene and the resulting oil was shaken in 400 ml of 10% sodium hydroxide solution. The suspended tan solid was collected by filtration, washed thrice with 100 ml portions of water, and air dried to give 9.7 g (99%) of crude product. A one gram portion was recrystallized from benzene/petroleum ether to give 100 ml of cream colored solid, m.p. 159°–161° C.

Analysis Calculated for $C_{19}H_{23}N_3O$: C,73.76; H,7.49; N,13.58

Found: C,73.65; H,7.44; N,13.48

Preparation 9

N-[4-(Piperazinyl)phenyl]acetamide.

This compound was prepared by the hydrogenation of 7.7 (0.025 mole) of N-[4-[4-(phenylmethyl)-1-piperazinyl]phenyl]acetamide in 100 ml of methanol using palladium on carbon as the catalyst. The solution was filtered and the filtrate concentrated under reduced pressure to give an oil which crystallized. The solid was dissolved in a minimum amount of a methylene chloride/10% methanol solution and passed through a 100 g Florisil ® column. The desired fractions were concentrated to an oil under reduced pressure which crystallized to give 3.1 g (56%) crude product. A 0.5 g portion was recrystallized from methanol/petroleum ether to give cream colored solid, m.p. 191°–193° C.

Analysis: Calculated for $C_{12}H_{17}N_3O$: C,65.73; H,7.81; N,19.16

Found: C,65.64; H,7.75; N,19.10

Preparation 10

4-(1-Piperazinyl)benzoic acid ethyl ester monohydrochloride.

To 3.1 g (0.015 mole) of 4-(1-piperazinyl)benzamide suspended in 5.0 ml (0.09 mole) of 95% ethyl alcohol was added dropwise 3.0 ml (0.06 mole) of 90% sulfuric acid under ice bath temperature. The mixture was heated at reflux for 5 hr and then neutralized with 10% sodium hydroxide under ice bath temperature. The suspended solid (starting material) was collected by filtration and the filtrate was extracted thrice with 25 ml portions of benzene. The combined benzene extracts were dried (magnesium sulfate) and concentrated under reduced pressure to give a golden oil. The hydrochloride was formed in 2-propanol saturated with hydrogen chloride and the collected solid, 1.1 g (31%), was recrystallized from 2-propanol to give 0.5 g of white crystalline solid, m.p. 203°–206° C.

Analysis: Calculated for $C_{13}H_{19}ClN_2O_2$: C,57.67; H,7.07; N,10.35

Found: C,57.52; H,7.13; N,10.38

Preparation 11

1-(1-Methylethyl)-3-azetidinamine, dihydrochloride.

The hydrochloride salt of 1-isopropyl-3-azetidinol (168 g; 1 mole) was partitioned between dilute sodium hydroxide and 700 ml of benzene. The benzene solution was dried over anhydrous sodium sulfate and concentrated to one half volume. The volume was made back to 700 ml with dry benzene and 110 g (1.1 mole) of triethylamine added. To this was added dropwise 115 g (1 mole) of methanesulfonyl chloride while cooling with an ice bath. The mixture was stirred at room temperature for one hour and filtered. The filter cake was washed twice with 100 ml of benzene and all the benzene filtrates combined. The benzene filtrate was extracted with 300 ml of 4N hydrochloric acid followed by 100 ml of water. The aqueous extracts were combined and the pH adjusted to 7 with sodium hydroxide. The solution was treated with 65 g (1 mole) of sodium azide and heated to reflux for 20 hr and cooled to room temperature with an ice bath. A solution (673 ml) of 23% aqueous ammonium sulfide was added while cooling with an ice bath to 30° C. and the solution was stirred at room temperature for 6 hr. The solution was continuously extracted with chloroform for 35 hr. (The condenser became plugged overnight and the pressure caused a joint to open and an unknown amount of material was lost). The chloroform was concentrated and distilled. Yield 18.5 g, b.p. 70°–80° C./20–30 mm. Two grams of the distillate was dissolved in ethanol and treated with ethereal hydrogen chloride. The resulting crystals were recrystallized from ethanol, yield of title compound from the 2 g sample was 1.35 g, m.p. 167°–170° C.

Analysis: Calculated for $C_6H_{16}N_2Cl_2$: C,38.52; H,8.62; N,14.97

Found: C,38.63; H,8.69; N,14.95

The synthesis of novel compounds of Formula I of the present invention is exemplified more fully in the following examples. Structures of the compounds of the examples are illustrated in Table 2. The scope of the invention is not limited to the examples presented, however.

EXAMPLE 1

4-(3-Chlorophenyl)-N-[2-(dimethylamino)ethyl]-1-piperazinecarboxamide maleate [1:1].

A 25 g (0.093 mole) sample of 1-(3-chlorophenyl) piperazine dihydrochloride was partitioned between methylene chloride and dilute sodium hydroxide. The organic layer was dried with anhydrous sodium sulfate and allowed to stand over Type 4A molecular sieves for three days.

In a separate flask 7.44 g (0.093 mole) of unsymdimethylethylenediamine was added dropwise to a stirred suspension of 15 g (0.093 mole) of 1,1'-carbonyldiimidazole in 150 ml of methylene chloride while cooling to $-10°$ to $-7°$ C. The cooling bath was removed and the solution was stirred 30 minutes. The solution was recooled to $-10°$ C. and the above prepared solution of the piperazine was added dropwise. The solution was heated to reflux for 5 hr, treated with 200 ml of chloroform and extracted with dilute hydrochloric acid. The acid layer was made basic with sodium hydroxide and extracted with chloroform, which was dried over sodium sulfate and concentrated. The residue was chromatographed by the dry column technique using alumina and eluting with chloroform. The product was extracted from the alumina with methanol which was concentrated and the residue distilled on a molecular still at 150° C./0.1 mm.

The distillate was treated with two molar equivalents of maleic acid in isopropyl alcohol and the resulting solid was recrystallized from the same solvent. Yield of title compound was 5 g (13%), m.p. 96°–103° C.

Analysis: Calculated for $C_{19}H_{27}O_5N_4Cl$: C,53.46; H,6.38; N,13.12

Found: C,53.22; H,6.28; N,12.34

EXAMPLE 2

4-(3-Chlorophenyl)-N-[2-(diethylamino)ethyl]-1-piperazinecarboxamide oxalate hydrate [1:1:0.5].

A solution of 11.6 g (0.1 mole) of unsym-diethyl ethylenediamine in 100 ml of dry tetrahydrofuran (THF) was added to a stirred solution of 18.2 g (0.11 mole) of 1,1'-carbonyldiimidazole in 100 ml of dry THF and the solution stirred for 1 hr at room temperature.

A sample of 25 g (0.093 mole) of 1-(3-chlorophenyl) piperazine hydrochloride was partitioned between toluene and dilute sodium hydroxide. The toluene was dried over anhydrous sodium sulfate and concentrated. The residue was dissolved in 50 ml of dry THF and added to the above prepared THF solution. The resulting solution was refluxed for 18 hr and concentrated. The residue was partitioned between 50% ethylacetate-50% isopropyl ether and dilute sodium hydroxide. The organic layer was dried over anhydrous sodium sulfate and concentrated. The residue was dissolved in 150 ml of methylene chloride and washed 6 times with 150 ml portions of water to remove the imidazole. The methylene chloride was concentrated. The residue was dissolved in isopropyl alcohol and treated with oxalic acid. A small amount of isopropyl ether was added and the milky mixture treated with charcoal and filtered. The resulting crystals were collected. Yield of title compound was 6 g (14%), m.p. 103°–105° C.

Analysis: Calculated for $C_{38}H_{60}N_8Cl_2O_{11}$: C,52.11; H,6.90; N,12.79

Found: C,52.10; H,6.72; N,12.60

EXAMPLE 3

N-[2-(Diethylamino)ethyl]-4-phenyl-1-piperazine-carboxamide oxalate [1:1].

A solution of 1,1'-carbonyldiimidazole (11.4 g, 0.07 mole) and unsym-diethylethylenediamine (6.96 g, 0.06 mole) in 250 ml of tetrahydrofuran was stirred at room temperature for 2-½ hours. 1-Phenylpiperazine (8.10 g, 0.05 mole) in 150 ml of tetrahydrofuran was added dropwise. The resulting solution was heated overnight at gentle reflux. The reaction mixture was stripped to dryness and partitioned between diethyl ether and water. Removal of ether gave an oil. The oil was dissolved in diethyl ether, and the ether layer was extracted with 1N sulfuric acid. The acidic layer was made alkaline and extracted with chloroform; removal of chloroform gave an oil. The oil was converted to the oxalate salt in methanol-diethyl ether mixture and recrystallized from isopropanol-isopropyl ether to give 2.44 g (12.5%) of white solid, m.p. 87.5°–89° C.

Analysis: Calculated for $C_{19}H_{30}N_4O_5$: C,57.85; H,7.67; N,14.20

Found: C,57.62; H,7.68; N,13.97

EXAMPLE 4

N-[2-(Diethylamino)ethyl]-4-phenyl-1-piperazinecarboxamide oxalate hydrate [1:1:1].

To a solution of 9.8 g (0.06 mole) of 1,1'-carbonyldiimidazole in 50 ml of tetrahydrofuran (THF) was added a solution of 5.8 g (0.05 mole) of unsym-diethylethylenediamine in 50 ml of THF and the reaction mixture was stirred for 2 hr at ambient temperature. A solution of 6.5 g (0.04 mole) of 1-phenylpiperazine in 100 ml of THF was added and the reaction mixture was heated at reflux for 18 hr. The solution was concentrated under reduced pressure and the residue was dissolved in 100 ml of benzene. The solution was washed with three 100 ml portions of water and brine, dried over anhydrous sodium sulfate and concentrated under reduced pressure to give 10.0 g (82%) of a yellow oil. The oil was converted to the oxalic acid salt in a solvent system of methanol, ethyl acetate, and ethyl ether. The solid was recrystallized from acetone to give 4.8 g (38%) of title compound as a white powder, m.p. 105°–108° C.

Analysis: Calculated for $C_{19}H_{30}N_4O_5 \cdot H_2O$: C,55.33; H,7.82; N,13.58

Found: C,55.48; H,7.38; N,13.26

EXAMPLE 5

N-[3-(Dimethylamino)propyl]-4-phenyl-1-piperazinecarboxamide.

To a solution of 5.7 g (0.035 mole) of 1,1'-carbonyldiimidazole in 75 ml of tetrahydrofuran (THF) was added a solution of 3.5 g (0.034 mole) of 3-dimethylaminopropylamine in 75 ml of THF and the reaction mixture was stirred at ambient temperature for 1.5 hr. A solution of 4.9 g (0.03 mole) of 1-phenylpiperazine in 50 ml of THF was added and the reaction mixture was heated at reflux for 20 hr. The solution was concentrated under reduced pressure and the residue was dissolved in 150 ml of benzene. The solution was washed thrice with 50 ml portions of water and once with brine, dried over anhydrous sodium sulfate and concentrated under reduced pressure to give an oil as residue which crystallized upon standing. The solid was triturated with petroleum ether (30°–60° C.), collected by filtration and recrystallized from cyclohexane to yield 5.0 g (57%) of title compound as a white solid, m.p. 91°–95° C.

Analysis: Calculated for $C_{16}H_{26}N_4O$: C,66.17; H,9.02; N,19.29

Found: C,66.23; H,9.07; N,19.22

EXAMPLE 6

4-Phenyl-N-[2-(1-pyrrolidinyl)ethyl]-1-piperazine-carboxamide.

This compound was prepared according to the procedure used to synthesize the compound of Example 5. A mixture of 5.7 g (0.035 mole) of 1,1'-carbonyldiimidazole, 3.9 g (0.034 mole) of N-(2-aminoethyl)pyrrolidine, and 4.9 g (0.03 mole) of 1-phenylpiperazine in a total of 200 ml of tetrahydrofuran gave 5.4 g (59%) of the title compound as a white powder, m.p. 81.5°–84° C., after recrystallizing from diisopropyl ether.

Analysis: Calculated for $C_{17}H_{26}H_4O$: C,67.52; H,8.67; N,18.53

Found: C,67.73; H,8.69; N,18.73

EXAMBLE 7

4-Phenyl-N-[2-(1-piperidinyl)ethyl]-1-piperazine-carboxamide.

This compound was prepared according to the procedure used to synthesize the compound of Example 5. A mixture of 5.7 g (0.035 mole) of 1,1'-carbonyldiimidazole, 4.4 g (0.034 mole) of N-(2-aminoethyl)piperidine and 4.9 g (0.03 mole) of 1-phenylpiperazine in a total of 200 ml of tetrahydrofuran gave 2.3 g (24%) of title compound as a white solid, m.p. 64°–67° C. after recrystallization from diethyl ether.

Analysis: Calculated for $C_{18}H_{28}N_4O$: C,68.32; H,8.92; N,17.71 or as ¼ hydrate: $C_{18}H_{28}N_4O.0.25\ H_2O$: C,67.36; H,8.95; N,17.46

Found: C,67.42; H,8.81; N,17.54

EXAMPLE 8

N-[2-(Dimethylamino)ethyl]-4-phenyl-1-piperazine-carboxamide.

This compound was prepared according to the procedure used to synthesize the compound of Example 5. A mixture of 5.7 g (0.035 mole) of 1,1'-carbonyldiimidazole, 3.0 g (0.034 mole) of unsym-dimethylethylenediamine and 4.9 g (0.03 mole) of 1-phenylpiperazine in a total of 200 ml of tetrahydrofuran gave 3.6 g (43%) of title compound as a white powder, m.p. 88°–90° C., after recrystallization from diisopropyl ether.

Analysis: Calculated for $C_{15}H_{24}N_4O$: C,65.19; H,8.75; N,20.27

Found: C,65.12; H,8.76; N,20.34

EXAMPLE 9

N-[2-(Hexahydro-1H-azepin-1-yl)ethyl]-4-phenyl-1-piperazinecarboxamide hydrochloride [1:2].

To a solution of 5.0 g (0.03 mole) of 1,1'-carbonyldiimidazole in 75 ml of tetrahydrofuran (THF) was added a solution of 4.0 g (0.028 mole) of N-(2-aminoethyl)homopiperidine in 75 ml of THF, and the reaction mixture was stirred at ambient temperature for 1.5 hr. A solution of 5.0 g (0.03 mole) of 1-phenylpiperazine in 50 ml of THF was added, and the reaction mixture was heated at reflux for 20 hr. The solution was concentrated under reduced pressure, and the residue was dissolved in 150 ml of benzene. The solution was washed thrice with 50 ml portions of water and once with brine, dried over anhydrous sodium sulfate and concentrated under reduced pressure to give an oil, which was converted to the hydrochloride with ethereal hydrogen chloride. The collected solid was recrystallized from 2-propanol to yield 6.7 g (53%) of title compound as a white solid, m.p. 190°–193° C.

Analysis: Calculated for $C_{19}H_{32}Cl_2N_4O$: C,56.57; H,8.00; N,13.89

Found: C,56.31; H,8.04; N,13.80

EXAMPLE 10

N-[2-(Diethylamino)ethyl]-4-(2-pyridinyl)-1-piperazine carboxamide, hydrochloride [1:2].

This compound was prepared according to the procedure used to synthesize the compound of Example 9. A mixture of 5.0 g (0.03 mole) of 1',1'-carbonyldiimidazole, 3.6 g (0.03 mole) of unsym-diethylethylenediamine, and 5.0 g (0.03 mole) of 1-(2-pyridinyl)-piperazine in a total of 200 ml of tetrahydrofuran gave an oil as residue. The hydrochloride was formed in ethereal hydrogen chloride and the collected solid was recrystallized from methanol-ethyl ether to yield 7.3 g (63%) of title compound as a white solid, m.p. 183°–185° C.

Analysis: Calculated for $C_{16}H_{29}Cl_2N_5O$: C,50.79; H,7.73; N,18.51

Found: C,50.45; H,7.77; N,18.47

EXAMPLE 11

N-[2-(Dimethylamino)ethyl]-4-(4-fluorophenyl)-1-piperazinecarboxamide.

To a solution of 6.3 g (0.04 mole) of 1,1'-carbonyldiimidazole in 50 ml of tetrahydrofuran (THF) was added a solution of 3.4 g (0.04 mole) of unsym-dimethylethylenediamine in 75 ml of THF and the reaction mixture was stirred at ambient temperature for 1.5 hr. A solution of 7.0 g (0.04 mole) of 1-(4-fluorophenyl)piperazine in 50 ml of THF was added and the reaction mixture was heated at reflux for 20 hr. The solution was concentrated under reduced pressure and the residue was dissolved in 150 ml of benzene. The solution was washed thrice with 50 ml portions of water and once with brine, dried over anhydrous sodium sulfate and concentrated under reduced pressure to give an oil which solidified. After trituration with petroleum ether (30°–60° C.), the collected solid was recrystallized from isopropyl alcohol/hexane to yield 7.8 g (68%) of title compound as a crystalline, white solid, m.p. 99°–101° C.

Analysis: Calculated for $C_{15}H_{23}FN_4O$: C,61.20; H,7.87; N,19.03

Found: C,61.20; H,7.90; N,19.25

EXAMPLE 12

N-[2-(Diethylamino)ethyl]-4-(4-fluorophenyl)-1-piperazinecarboxamide, hydrochloride [1:2].

To a solution of 6.3 g (0.04 mole) of 1,1'-carbonyldiimidazole in 75 ml of tetrahydrofuran (THF) was added a solution of 4.5 g (0.04 mole) of unsym-diethylethylenediamine in 75 ml of THF and the reaction mixture was stirred at ambient temperature for 3 hr. A solution of 7.0 g (0.04 mole) of 1-(4-fluorophenyl)piperazine in 50 ml of THF was added and the reaction mixture was heated at reflux for 20 hr. The solution was concentrated under reduced pressure and the residue was dissolved in 150 ml of benzene. The solution was washed thrice with 50 ml portions of water and once with brine, dried over magnesium sulfate, and concentrated under reduced pressure to give an oil as residue. The hydrochloride was formed in ethereal hydrogen chloride and the collected solid was recrystallized twice from methanol/ethyl ether to yield 2.2 g (14%) of title compound as a white solid, m.p. 165°–167° C.

Analysis: Calculated for $C_{17}H_{29}Cl_2FN_4O$: C,51.65; H,7.39; N,14.17

Found: C,51.29; H,7.40; N,14.14

EXAMPLE 13

4-(2-Chlorophenyl)-N-[2-(dimethylamino)ethyl]-1-piperazinecarboxamide, hydrochloride [1:1].

This compound was prepared according to the procedure used to synthesize the compound of Example 11. A mixture of 4.9 g (0.03 mole) of 1,1′-carbonyldiimidazole, 2.6 g (0.03 mole) of unsym-diethylethylenediamine, and 5.9 g (0.03 mole) of 1-(2-chlorophenyl)piperazine in a total of 200 ml of tetrahydrofuran gave an oil as residue. The hydrochloride was formed in ethereal hydrogen chloride and the collected solid was recrystallized from methanol-ethyl ether to yield 3.4 g (33%) of title compound as a white solid, m.p. 185°–188° C.

Analysis: Calculated for $C_{15}H_{24}Cl_2N_4O$: C,51.88; H,6.97; N,16.13

Found: C,51.55; H,6.93; N,16.21

EXAMPLE 14

4-(4-Chlorophenyl)-N-[2-(dimethylamino)ethyl]-1-piperazinecarboxamide.

This compound was prepared according to the procedure used to synthesize the compound of Example 11. A mixture of 4.9 g (0.03 mole) of 1,1′-carbonyldiimidazole, 2.6 g (0.03 mole) of unsym-dimethylethylenediamine, and 5.9 g (0.03 mole) of 1-(4-chlorophenyl)piperazine in a total of 200 ml of tetrahydrofuran gave an oil which solidified when triturated with petroleum ether (30°–60° C.). The collected solid was recrystallized from 2-propanol-isopropyl ether to yield 6.1 g (66%) of the title compound as a white, crystalline solid, m.p. 125°–128° C.

Analysis: Calculated for $C_{15}H_{23}ClN_4O$: C,57.96; H,7.46; N,18.02

Found: C,57.88; H,7.48; N,17.90

EXAMPLE 15

N-[2-(Dimethylamino)ethyl]-4-(2-pyridinyl)-1′-piperazinecarboxamide hydrochloride [1:2].

This compound was prepared according to the procedure used to synthesize the compound of Example 11. A mixture of 4.9 g (0.03 mole) of 1,1′-carbonyldiimidazole, 2.6 g (0.03 mole) of unsym-dimethylethylenediamine, and 4.9 g (0.03 mole) of 1-(2-pyridinyl)piperazine ub a total of 200 ml of tetrahydrofuran gave an oil as residue. The hydrochloric acid salt was formed in ethereal hydrogen chloride and the collected solid was recrystallized from methanol-ethyl ether and then 2-propanol to yield 1.1 g (11%) of the title compound as a white solid, m.p. 208°–210° C.

Analysis: Calculated for $C_{14}H_{25}Cl_2N_5O$: C,48.00; H,7.19; N,19.99

Found: C,47.60; H,7.47; N,19.98

EXAMPLE 16

N-[2-(Dimethylamino)ethyl]-4-(4-methoxyphenyl)-1-piperazinecarboxamide.

This compound was prepared according to the procedure used to synthesize the compound of Example 11. A mixture of 4.9 g (0.03 mole) of 1,1′-carbonyldiimidazole, 2.6 g (0.03 mole) of unsym-dimethylethylenediamine, and 5.8 g (0.03 mole) of 1-(4-methoxyphenyl)piperazine in a total of 200 ml of tetrahydrofuran gave an oil which solidified. After trituration with petroleum ether (30°–60° C.), the collected solid was recrystallized from cyclohexanebenzene to yield 2.2 g (24%) of the title compound as a white, crystalline solid, m.p. 79°–82° C.

Analysis: Calculated for $C_{16}H_{26}N_4O_2$: C,62.72; H,8.55; N,18.28

Found: C,62.61; H,8.69; N,18.35

EXAMPLE 17

N-[2-(Dimethylamino)ethyl]-4-(3-methoxyphenyl)-1-piperazinecarboxamide.

This compound was prepared according to the procedure used to synthesize the compound of Example 11. A mixture of 4.9 g (0.03 mole) of 1,1′-carbonyldiimidazole, 2.6 g (0.03 mole) of unsym-dimethylethylenediamine, and 5.8 g (0.03 mole) of 1-(3-methoxyphenyl)piperazine in a total of 200 ml of tetrahydrofuran gave an oil which solidified. After trituration with petroleum ether (30°–60° C.), the collected solid was recrystallized from cyclohexanebenzene to yield 4.7 g (51%) of the title compound as a white crystalline solid, m.p. 70°–72° C.

Analysis: Calculated for $C_{16}H_{26}N_4O_2$: C,62.72; H,8.55; N,18.28

Found: C,62.79; H,0.88; N,18.36

EXAMPLE 18

N-[2-(Dimethylamino)ethyl]-4-(3,4,5-trimethoxyphenyl)-1-piperazinecarboxamide hydrochloride [1:2].

This compound was prepared according to the procedure used to synthesize the compound of Example 11. A mixture of 2.4 g (0.015 mole) of 1,1′-carbonyldiimidazole, 13 g (0.015 mole) of unsym-dimethylethylenediamine and 3.8 g (0.025 mole) of 1-(3,4,5-trimethoxyphenyl)piperazine in a total volume of 100 ml of tetrahydrofuran gave an oil as residue. The hydroxhloride was formed in ethereal hydrogen chloride and the collected solid was recrystallized from methanol-ethyl ether to yield 3.7 g (56%) of the title compound as a white solid, m.p. 205°–208° C.

Analysis: Calculated for $C_{18}H_{32}Cl_2N_4O_4$: C,49.20; H,7.34; N,12.75

Found: C,48.98; H,7.42; N,12.65

EXAMPLE 19

4-(3,4-Dichlorophenyl)-N-[2-(dimethylamino)ethyl]-1-piperazinecarboxamide.

This compound was prepared according to the procedure used to synthesize the compound of Example 11. A mixture of 2.5 g (0.025 mole) of 1,1′-carbonyldiimidazole, 1.4 g (0.015 mole) of unsym-dimethylethylenediamine and 3.6 g (0.015 mole) of 1-(3,4-dichlorophenyl)piperazine in a total of 100 ml of tetrahydrofuran gave an oil which solidified when triturated with cyclohexane. White solid, the title compound, in the amount of 4.0 g (75%) was collected, m.p. 80°–83° C.

EXAMPLE 20

N-[2-(Dimethylamino)ethyl]-4-[3-(trifluoromethyl)-phenyl]-1-piperazinecarboxamide hydrochloride.

This compound was prepared according to the procedure used to synthesize the compound of Example 11. A mixture of 4.9 g (0.03 mole) of 1,1'-carbonyldiimidazole, 2.6 g (0.03 mole) of unsym-dimethylethylenediamine and 6.9 g (0.03 mole) of 1-(α,α,α-trifluoro-m-tolyl)piperazine in a total volume of 200 ml of tetrahydrofuran gave an oil as residue. The hydrochloride was formed in ethereal and the collected solid was recrystallized from methanol to yield 5.9 g (47%) of the title compound as a white solid, m.p. 205°–208° C.

Analysis: Calculated for $C_{16}H_{25}Cl_2F_3N_4O$: C,45.93; H,13.45; N,6.12

Found: C,46.05; H,13.43; N,6.04

EXAMPLE 21

N-[2-(Dimethylamino)ethyl]-4-(4-methylphenyl)-1-piperazinecarboxamide.

This compound was prepared according to the procedure used to synthesize the compound of Example 11. A mixture of 1.9 g (0.01 mole) of 1,1'-carbonyldiimidazole, 1.0 g (0.01 mole) of unsym-dimethylethylenediamine, and 2.0 g (0.1 mole) of 1-(4-methylphenyl)piperazine in a total volume of 100 ml of tetrahydrofuran gave an oil which solidified. The solid was triturated with petroleum ether (30°–60° C.) to give 1.5 g (47%) of the title compound as a white solid, m.p. 85°–88° C.

Analysis: Calculated for $C_{16}H_{26}N_4O$: C,66.17; H,9.02; N,19.29

Found: C,65.92; H,9.03; N,19.35

EXAMPLE 22

4-(3,4-Dimethoxyphenyl)-N-[2-(dimethylamino)ethyl]-1-piperazinecarboxamide hydrochloride [1:2].

This compound was prepared according to the procedure used to synthesize the compound of Example 11. A mixture of 1.6 g (0.01 mole) of 1,1'-carbonyldiimidazole, 0.87 g (0.01 mole) of unsym-dimethylethylenediamine, and 2.2 g (0.01 mole) of 1-(3,4-dimethoxyphenyl)piperazine in a total volume of 50 ml of tetrahydrofuran gave an oil as residue. The hydrochloride was formed in ethereal hydrogen chloride and the collected solid was recrystallized twice from methanolethyl ether to yield 2.3 g (57%) of the title compound as an off-white solid, m.p. 208°–210° C.

Analysis: Calculated for $C_{17}H_{30}Cl_2N_4O_3$: C,49.88; H,7.39; N,13.69

Found: C,49.67; H,7.44; N,13.73

EXAMPLE 23

N-[2-(Dimethylamino)ethyl]-4-(2-methoxyphenyl)-1-piperazinecarboxamide.

This compound was prepared according to the procedure used to synthesize the compound of Example 11. A mixture of 4.9 g (0.03 mole) of 1,1'-carbonyldiimidazole, 2.6 g (0.03 mole) of unsym-dimethylethylenediamine and 5.8 g (0.03 mole) of 1-(2-methoxyphenyl)piperazine in a total volume of 200 ml of tetrahydrofuran gave an oil which solidified. After trituration with petroleum ether (30°–60° C.), the collected solid was recrystallized from benzene-petroleum ether to yield 4.5 g (49%) of the title compound as an off-white solid, m.p. 98°–100° C.

Analysis: Calculated for $C_{16}H_{26}N_4O_2$: C,62.72; H,8.55; N,18.29

Found: C,62.45; H,8.59; N,18.27

EXAMPLE 24

N-[2-(Dimethylamino)ethyl]-4-(4-nitrophenyl)-1-piperazinecarboxamide.

This compound was prepared according to the procedure used to synthesize the compound of Example 11. A mixture of 5.5 g (0.03 mole) of 1,1'-carbonyldiimidazole, 3.0 g (0.03 mole) of unsym-dimethylethylenediamine and 7.0 g (0.03 mole) of 1-(4-nitrophenyl)piperazine in a total volume of 200 ml of tetrahydrofuran gave an oil that solidified. The solid was recrystallized from benzene to give 5.8 g (54%) of the title compound as a yellow solid, m.p. 115°–120° C.

Analysis: Calculated for $C_{15}H_{23}N_5O_3$: C,56.06; H,7.21; N,21.79

Found: C,55.02; H,7.13; N,21.98

EXAMPLE 25

N-[2-(Dimethylamino)ethyl]-4-[4-(dimethylamino)-phenyl]-1-piperazinecarboxamide hydrochloride [1:3].

This compound was prepared by the hydrogenation of 1.7 g (0.005 mole) of N-[2-(dimethylamino)ethyl]-4-(4-nitrophenyl)-1-piperazinecarboxamide in the presence of two equivalents (0.80 mole) of 37% formalin using palladium on carbon as the catalyst and 200 ml of methanol as the solvent. The mixture was filtered through Celite ® and the filtrate concentrated under reduced pressure to give an oil. The hydrochloride was formed in ethereal hydrogen chloride and recrystallized from methanol-ethyl ether to give 0.4 g (18%) of the title compound as a white solid, m.p. 221°–223° C.

Analysis: Calculated for $C_{17}H_{32}Cl_3N_5O$: C,47.61; H,7.52; N,16.33

Found: C,47.44; H,7.63; N,16.60

EXAMPLE 26

N-[2-(Dimethylamino)ethyl]-4-(3-fluorophenyl)-1-piperazinecarboxamide hydrochloride [1:2].

This compound was prepared according to the procedure used to synthesize the compound of Example 11. A mixture of 2.4 g (0.015 mole) of 1-(3-fluorophenyl)piperazine and 1.3 g (0.015 mole) of unsym-dimethyethylenediamine in a total volume of 200 ml of tetrahydrofuran gave a clear oil as residue. The hydrochloride was formed in ethereal hydrogen chloride and the collected solid was recrystallized from methanol-ethyl ether to give 2.7 g (50%) of the title compound as a white solid, m.p. 200°–203° C.

Analysis: Calculated for $C_{15}H_{25}FN_4O$: C,49.05; H,6.86; N,15.25

Found: C,49.30; H,7.01; N,15.64

EXAMPLE 27

N-[2-(Dimethylamino)ethyl]-4-(2-fluorophenyl)-1-piperazinecarboxamide hydrochloride hydrate [1:2:0.5].

This compound was prepared according to the procedure used to synthesize the compound of Example 11. A mixture of 1.5 g (0.009 mole) of 1,1'-carbonyldiimidazole, 0.8 g (0.009 mole) of unsym-dimethyethylenediamine and 1.7 g (0.009 mole) of 1-(2-fluorophenyl)piperazine in a total volume of 200 ml of tetrahydrofuran gave an oil as residue. The hydrochloride was formed in ethereal hydrogen chloride and the collected solid was recrystallized from methanol-water-ethyl ether to give the title compound as a white crystalline solid, m.p. 146°–150° C.

Analysis: Calculated for $C_{15}H_{25}Cl_2FN_4O\cdot 0.5\ H_2O$: C,47.88; H,6.96; N,14.89
Found: C,47.98; H,6.85; N,15.17

EXAMPLE 28

N-[2-(Dimethylamino)ethyl]-4-(2-fluorophenyl)-1-piperazinecarboxamide dihydrochloride.

This compound was prepared according to the procedure used to synthesize the compound of Example 11. A mixture of 2.2 g (0.01 mole) of 1,1'-carbonyldiimidazole, 2.2 g (0.01 mole) of unsym-dimethylethylenediamine and 2.5 g (0.01 mole of 1-(2-fluorophenyl)piperazine in a total volume of 100 ml of tetrahydrofuran gave an oil as residue. The hydrochloride was formed in ethereal hydrogen chloride and the solid recrystallized from methanol-diethyl ether to give 2.3 g (46%) of title compound as a white solid, m.p. 153°–155° C.

Analysis: Calculated for: C,49.05; H,6.86; N,15.25
Found: C,48.86; H,6.88; N,15.17

EXAMPLE 29

4-(4-Fluorophenyl)-N-[2-(1-pyrrolidinyl)ethyl]-1-piperazinecarboxamide.

This compound was prepared according to the procedure used to synthesize the compound of Example 11. A mixture of 10.4 g (0.064 mole) of 1,1'-carbonyldiimidazole, 7.3 g (0.064 mole) of N-(2-aminoethyl)pyrrolidine and 11.5 g (0.064 mole) of 1-(4-fluorophenyl)piperazine in a total volume of 500 ml of tetrahydrofuran gave an oil that solidified when triturated with petroleum ether. The collected solid was recrystallized from benzene to give 2.8 g of the title compound as a white solid, m.p. 100°–102° C.

Analysis: Calculated for $C_{17}H_{25}FN_4O$: C,63.73; H,7.87; N,17.49
Found: C,63.46; H,8.06; N,17.28

EXAMPLE 30

4-(4-Fluorophenyl)-N-[2-(1-pyrrolidinyl)ethyl]-1-piperazinecarboxamide, hydrochloride [1:2].

This compound was prepared according to the procedure used to synthesize the compound of Example 11. A mixture of 10.4 g (0.064 mole) of 1,1'-carbonyldiimidazole, 7.3 g (0.064 mole) of N-(2-aminoethyl)pyrrolidine and 11.5 g (0.064 mole) of 1-(4-fluorophenyl)-piperazine in a total volume of 500 ml of tetrahydrofuran gave an oil that solidified when triturated with petroleum ether. The collected solid was recrystallized from benzene to give 2.8 g of the free base of the title compound as a white solid, m.p. 100°–102° C. The filtrate was converted to the hydrochloride with ethereal hydrogen chloride and the collected solid was recrystallized from methanol-ethyl ether to give 7.4 g of the title compound as a white solid; m.p. 197°–200° C. The total yield of free base and salt was 43%.

Analysis: Calculated for $C_{17}H_{27}Cl_2FN_4O$: C,51.91; H,6.92; N,14.24
Found: C,51.57; H,6.94; N,14.32

EXAMPLE 31

4-(4-Cyanophenyl)-N-[2-(dimethylamino)ethyl]-1-piperazinecarboxamide hydrochloride [1:2].

This compound was prepared according to the procedure used to synthesize the compound of Example 11. A mixture of 2.6 g (0.016 mole) of 1,1'-carbonyldiimidazole, 1.4 g (0.016 mole) of unsym-dimethylethylenediamine and 3.0 g (0.16 mole) of 1-(4-cyanophenyl)piperazine in a total volume of 250 ml of tetrahydrofuran gave an oil. The hydrochloride was formed in ethereal hydrogen chloride and the solid recrystallized from methanol-ethyl ether to give 1.2 g (20%) of the title compound as a white solid; m.p. 161°–164° C.

Analysis: Calculated for $C_{16}H_{25}Cl_2N_5O$: C,51.34; H,6.73; N,18.71
Found: C,51.33; H,6.91; N,18.64

EXAMPLE 32

4-(4-Bromophenyl)-N-[2-(dimethylamino)ethyl]-1-piperazinecarboxamide.

This compound was prepared according to the procedure used to synthesize the compound of Example 11. A mixture of 4.8 g (0.03 mole) of 1,1'-carbonyldiimidazole, 2.6 g (0.03 mole) of unsym-dimethylethylenediamine, and 6.2 g (0.03 mole) of 1-(4-bromophenyl)piperazine in a total of 200 ml of tetrahydrofuran gave a pale yellow semisolid. The material was triturated with ethyl ether to give 7.7 g (84%) of the title compound as a white solid, m.p. 133°–135° C.

Analysis: Calculated for $C_{15}H_{23}N_4BrO$: C,50.71; H,6.53; N,15.77
Found: C,50.63; H,6.52; N,15.90

EXAMPLE 33

4-(4-Aminophenyl)-N-[2-(dimethylamino)ethyl]-1-piperazinecarboxamide hydrochloride [1:3].

This compound was prepared by the catalytic hydrogenation (palladium on carbon) of 8.0 g (0.02 mole) of N-[2-(dimethylamino)ethyl]-4-(4-nitrophenyl)-1-piperazinecarboxamide in 150 ml of methanol for 1 hour. The filtered mixture was concentrated under reduced pressure to give an oil as residue. The oil was converted to the hydrochloride in ethereal hydrogen chloride. The solid was recrystallized from methanol-water to give 2.0 g (20%) of the title compound as a white solid, m.p. 114°–116° C.

Analysis: Calculated for $C_{15}H_{28}Cl_3N_5O$: C,44.95; H,7.04; N,17.47
Found: C,44.88; H,7.07; N,17.41

EXAMPLE 34

4-(4-Acetylphenyl)-N-[2-(dimethylamino)ethyl]-1-piperazinecarboxamide monohydrochloride.

This compound was prepared according to the procedure used to synthesize the compound of Example 11. A mixture of 4.9 g (0.03 mole) of 1,1'-carbonyldiimidazole, 2.5 g (0.03 mole) of unsym-dimethylethylenediamine and 6.1 g (0.03 mole) of 4-piperazinoacetophenone in a total volume of 200 ml of tetrahydrofuran gave an oil as residue. The oil was eluted through a 200 g silica gel column with an 80% methylene chloride-19.8% methanol-0.2% ammonium hydroxide mixture. The product fractions were concentrated under reduced pressure to give an oil which was partitioned between water and chloroform. The chloroform layer was separated, dried over magnesium sulfate and concentrated under reduced pressure to an oil. The hydrochloride was formed in ethereal hydrogen chloride and the solid recrystallized from methanol-diethyl ether to give 3.7 g of product as a yellow solid. The product was recrystallized again from 2-propanol-water to give 2.0 g (19%) of the title compound as a light cream solid, m.p. 221°–223° C.

Analysis: Calculated for $C_{17}H_{27}ClN_4O_2$: C,57.54; H,7.67; N,15.79

Found: C,57.25; H,7.72; N,15.53

EXAMPLE 35

4-[4-(Aminocarbonyl)phenyl]-N-[2-(dimethylamino)ethyl]-1-piperazinecarboxamide.

This compound was prepared according to the procedure used to synthesize the compound of Example 11. A mixture of 3.1 g (0.019 mole) of 1,1'-carbonyldiimidazole, 1.7 g (0.019 mole) of unsym-dimethylethylenediamine and 3.9 g (0.019 mole) of 4-(1-piperazinyl)benzamide in a total volume of 150 ml of tetrahydrofuran gave a suspended white solid. The collected solid was recrystallized from ethanol-benzene to give 1.2 g (20%) of the title compound as a white solid, m.p. 193°–195° C.

Analysis: Calculated for $C_{16}H_{25}N_5O_2$: C,60.17; H,7.89; N,21.93

Found: C,60.02; H,7.92; N,21.94

EXAMPLE 36

4-[4-[[[2-(Dimethylamino)ethyl]aminocarbonyl]-1-piperazinyl]-benzoic acid ethyl ester dihydrochloride.

This compound was prepared according to the procedure used to synthesize the compound of Example 11. A mixture of 2.6 g (0.016 mole) of 1,1'-carbonyldiimidazole, 1.4 g (0.016 mole) of unsym-dimethylethylenediamine and 3.8 g (0.016 mole) of 4-(1-piperazinyl)benzene acid ethyl ester in a total volume of 250 ml of tetrahydrofuran gave a cream colored solid. The hydrochloride was formed in 2-propanol saturated with hydrogen chloride and the collected solid was recrystallized from methanol-ethyl ether to give 4.8 g (71%) of the title compound as a white solid, m.p. 179°–182° C.

Analysis: Calculated for $C_{18}H_{30}Cl_2N_4O_3$: C,51.31; H,7.18; N,13.30

Found: C,51.01; H,7.26; N,13.30

EXAMPLE 37

4-[4-(Acetylamino)phenyl]-N-[2-(dimethylamino)ethyl]-1-piperazinecarboxamide hydrochloride [1:2].

This compound was prepared according to the procedure used to synthesize the compound of Example 11. A mixture of 2.0 g (0.009 mole) of N-[4-(1-piperazinyl)phenyl]acetamide, 0.8 g (0.009 mole) of unsym-dimethylethylenediamine and 1.5 g (0.009 mole) of 1,1'-carbonyldiimidazole in a total volume of 200 ml of tetrahydrofuran gave an oil as residue. Trituration of the oil with ethyl ether gave 1.2 g of a white solid. The solid was recrystallized from tetrahydrofuran to give 0.4 g of solid. The solid was converted to the hydrochloride in 2-propanol saturated with hydrogen chloride and the collected solid was recrystallized from 2-propanol to give 0.2 g (6%) of the title compound as a white solid, m.p. 216°–217° C.

Analysis: Calculated for $C_{17}H_{29}Cl_2N_5O_2$: C,50.25; H,7.19; N,17.23

Found: C,49.97; H,7.32; N,17.04

EXAMPLE 38

N-(1-Ethyl-3-piperidinyl)-4-phenyl-1-piperazinecarboxamide.

This compound was prepared according to the procedure of Example 5. A mixture of 5.7 g (0.035 mole) of 1,1'-carbonyldiimidazole, 4.4 g (0.034 mole) of 3-amino-1-ethylpiperidine and 4.9 g (0.030 mole) of 1-phenylpiperazine in a total of 200 ml of tetrahydrofuran gave 6.2 g (65%) of white solid, m.p. 100°–103° C. (diisopropyl ether).

Analysis: Calculated for $C_{18}H_{28}N_4O$: C,68.32; H,8.92; N,17.71

Found: C,68.08; H,8.89; N,17.61

EXAMPLE 39

4-(3-Chlorophenyl)-N-[2-(diethylamino)ethyl]-1-piperazinethiocarboxamide oxalate.

Following the procedure of Example 2 but substituting 1,1'-thiocarbonyldiimidazole for 1,1'-carbonyldiimidazole, the title compound is prepared from 1-(3-chlorophenyl)piperazine and unsym-diethylethylenediamine and oxalic acid.

EXAMPLE 40

4-Phenyl-N-[2-(1-azetidinyl)ethyl]-1-piperazinecarboxamide.

Following the procedure of Example 5, N-(2-aminoethyl)azetidine and 1,1'-carbonyldiimidazole are reacted together in tetrahydrofuran and the product thereof is reacted further with 1-phenylpiperazine to give the title compound.

EXAMPLE 41

4-Phenyl-N-(1,2,3,6-tetrahydropyridin-1-yl-ethyl)-1-piperazinecarboxamide.

Following the procedure of Example 5, N-(2-aminoethyl)-1,2,3,6-tetrahydropyridine and 1,1'-carbonyldiimidazole are reacted together in tetrahydrofuran and the product thereof is reacted further with 1-phenylpiperazine to give the title compound.

EXAMPLE 42

4-Phenyl-N-(morpholin-4-ylethyl)-1-piperazinecarboxamide.

Following the procedure of Example 5, N-(2-aminoethyl)morpholine and 1,1'-carbonyldiimidazole are reacted together in tetrahydrofuran and the product thereof is reacted further with 1-phenylpiperazine to give the title compound.

EXAMPLE 43

4-[4-[[[2-(Dimethylamino)ethyl]amino]carbonyl]-1-piperazinyl]benzoic acid sodium salt.

The title compound is prepared in aqueous solution by neutralization and hydrolysis of 4-[4-[[[2-(dimethylamino)ethyl]amino]carbonyl]-1-piperazinyl benzoic acid ethyl ester dihydrochloride in hot aqueous sodium carbonate solution. The free carboxylic acid derivative may be obtained by neutralizing with an acid such as hydrochloric acid.

EXAMPLES 44 a and b

When in the procedure of Example 5 the following are substituted for 3-amino-1-ethylpiperidine:
3-amino-1-ethylpyrrolidine, and
3-amino-1-ethylhomopiperidine,
there are obtained:
N-(1-ethyl-3-pyrrolidinyl)-4-phenyl-1-piperazine-carboxamide, and
N-(1-ethyl-3-homopiperidinyl)-4-phenyl-1-piperazine-carboxamide.

EXAMPLE 45

N-[1-Isopropyl-3-azetidinyl]-4-phenyl-1-piperazine-carboxamide.

Following the procedure of Example 5 and substituting 1-isopropyl-3-aminoazetidine for 3-dimethylaminopropylamine, the title compound is obtained.

TABLE 1

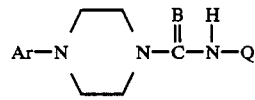

| Example No. | Ar | B | Q | Salt |
|---|---|---|---|---|
| 1 | 3-Cl—$C_6H_4$— | O | —$(CH_2)_2N(CH_3)_2$ | maleate |
| 2 | 3-Cl—$C_6H_4$— | O | —$(CH_2)_2N(C_2H_5)_2$ | oxalate, ½ $H_2O$ |
| 3 | $C_6H_5$— | O | —$(CH_2)_2N(C_2H_5)_2$ | oxalate |
| 4 | $C_6H_5$— | O | —$(CH_2)_2N(C_2H_5)_2$ | oxalate, 1 $H_2O$ |
| 5 | $C_6H_5$— | O | —$(CH_2)_3N(CH_3)_2$ | — |
| 6 | $C_6H_5$— | O | —$(CH_2)_2$-pyrrolidin-1-yl | — |
| 7 | $C_6H_5$— | O | —$(CH_2)_2$-piperidin-1-yl | — |
| 8 | $C_6H_5$— | O | —$(CH_2)_2N(CH_3)_2$ | — |
| 9 | $C_6H_5$— | O | —$(CH_2)_2$-homopiperidin-1-yl | 2 HCl |
| 10 | pyridin-2-yl | O | —$(CH_2)_2N(C_2H_5)_2$ | 2 HCl |
| 11 | 4-F—$C_6H_4$— | O | —$(CH_2)_2N(CH_3)_2$ | — |
| 12 | 4-F—$C_6H_4$— | O | —$(CH_2)_2N(C_2H_5)_2$ | 2 HCl |
| 13 | 2-Cl—$C_6H_4$— | O | —$(CH_2)_2N(CH_3)_2$ | HCl |
| 14 | 4-Cl—$C_6H_4$— | O | —$(CH_2)_2N(CH_3)_2$ | — |
| 15 | pyridin-2-yl | O | —$(CH_2)_2N(CH_3)_2$ | 2 HCl |
| 16 | 4-$OCH_3$—$C_6H_4$— | O | —$(CH_2)_2N(CH_3)_2$ | — |
| 17 | 3-$CH_3$—$C_6H_4$— | O | —$(CH_2)_2N(CH_3)_2$ | 2 HCl |
| 18 | 3,4,5-$(OCH_3)_3$—$C_6H_2$— | O | —$(CH_2)_2N(CH_3)_2$ | 2 HCl |
| 19 | 3,4-$(Cl_2)_2$—$C_6H_3$— | O | —$(CH_2)_2N(CH_3)_2$ | — |
| 20 | 3-$CF_3$—$C_6H_4$— | O | —$(CH_2)_2N(CH_3)_2$ | 2 HCl |
| 21 | 4-$CH_3$—$C_6H_4$— | O | —$(CH_2)_2N(CH_3)_2$ | — |
| 22 | 3,4-$(OCH_3)_2$—$C_6H_3$— | O | —$(CH_2)_2N(CH_3)_2$ | 2 HCl |
| 23 | 2-$OCH_3$—$C_6H_4$— | O | —$(CH_2)_2N(CH_3)_2$ | — |
| 24 | 4-$NO_2$—$C_6H_4$— | O | —$(CH_2)_2N(CH_3)_2$ | — |
| 25 | 4-[—$N(CH_3)_2$]—$C_6H_4$ | O | —$(CH_2)_2N(CH_3)_2$ | 3 HCl |
| 26 | 3-F—$C_6H_4$— | O | —$(CH_2)_2N(CH_3)_2$ | 2 HCl |
| 27 | 2-F—$C_6H_4$— | O | —$(CH_2)_2N(CH_3)_2$ | 2 HCl, ½ $H_2O$ |
| 28 | 2-F—$C_6H_4$— | O | —$(CH_2)_2N(CH_3)_2$ | 2 HCl |
| 29 | 4-F—$C_6H_4$— | O | —$(CH_2)_2$-pyrrolidin-1-yl | — |
| 30 | 4-F—$C_6H_4$— | O | —$(CH_2)_2$-pyrrolidin-1-yl | 2 HCl |
| 31 | 4-CN—$C_6H_4$— | O | —$(CH_2)_2N(CH_3)_2$ | 2 HCl |
| 32 | 4-Br—$C_6H_4$— | O | —$(CH_2)_2N(CH_3)_2$ | — |
| 33 | 4-$NH_2$—$C_6H_4$— | O | —$(CH_2)_2N(CH_3)_2$ | 3 HCl |
| 34 | 4-[C(O)$CH_3$]—$C_6H_4$— | O | —$(CH_2)_2N(CH_3)_2$ | HCl |
| 35 | 4-[C(O)$NH_2$]—$C_6H_4$ | O | —$(CH_2)_2N(CH_3)_2$ | — |
| 36 | 4-[C(O)O$C_2H_5$]—$C_6H_4$ | O | —$(CH_2)_2N(CH_3)_2$ | 2 HCl |
| 37 | 4-[NHC(O)$CH_3$]—$C_6H_4$ | O | —$(CH_2)_2N(CH_3)_2$ | 2 HCl |
| 38 | $C_6H_5$— | O | 1-$C_2H_5$-piperidin-3-yl | — |
| 39 | 3-Cl—$C_6H_4$— | S | —$(CH_2)_2N(C_2H_5)_2$ | oxalate |
| 40 | $C_6H_5$— | O | —$(CH_2)_2$-azetidin-1-yl | — |
| 41 | $C_6H_5$— | O | —$(CH_2)_2$—N⟨cyclic⟩ | — |
| 42 | $C_6H_5$— | O | —$(CH_2)_2$—N(morpholin-4-yl) | — |
| 43 | 4-(COO$^-$)—$C_6H_4$— | O | —$(CH_2)_2$—$N(CH_3)_2$ | $Na^+$ |
| 44 (a) | $C_6H_5$— | O | 1-$C_2H_5$-pyrrolidin-3-yl | — |
| 44 (b) | $C_6H_5$— | O | —$C_2H_5$-homopiperidin-3-yl | — |
| 45 | $C_6H_5$— | O | 1-[CH($CH_3$)$_2$]-azetidin-3-yl | — |

Pharmacology Methods

Antiallergy Screening Method - Rats

As stated above, the primary screening method used to demonstrate antiallergy properties of the compounds of Formula I is a modification of the procedure of R. R. Martel and J. Klicius, International Archives Allergy Appl. Immunology, Vol. 54, pp 205-209 (1977) which measures the effect of oral administration of the compound on the volume of a rat paw which was previously injected with anti-egg albumin serum following egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scrambler. Random number tables are used to determine the groups receiving the control, reference and test articles. On the test day, the right foot volume of each rat is determined plethysmographically using the hairline as the reference point. Volume of this foot is measured with a mercury filled tube that is connected to a P23A Statham ® pressure transducer that in turn is connected to a linear Cole Parmer ® recorder (Model No. 255). The instrument is adjusted so that a pen deflection of 50 mm is equivalent to 1 ml volume. Separately, the reference and test compounds and control articles are dissolved or suspended in 0.5% Tween 80 in distilled water. Sonification is used to facilitate dissolution or reduce particle size. The animals are dosed orally (10 ml/kg) at 1 hr prior to the intravenous injection of the antigen, 2 mg of egg albumin in 0.2 ml of sterile saline. Thirty minutes later the right foot volume is measured again and edema is determined by difference. Results are expressed as the average foot edema (ml)±S. D. A significant decrease ($p<0.05$) in the edema of the treated group from that of the control group is considered as indicative of antiallergic activity. The results are acceptable only if the group receiving the reference article shows a significant decrease in foot edema. The foot volume for each animal is measured twice, once prior to dosing and again 30 min following the intravenous administration of antigen. Data is analyzed with the Dunnett's t-test that compares several treated groups with a control group. Differences between groups are determined by the studentized Range Test. Regression analysis may be used to determine relative potency.

Guinea Pig Anaphylaxis Method

The method used to test antiallergy effectiveness of the compounds in guinea pigs as compared to other drugs is as follows:

Guinea pigs are first sensitized to egg albumin (EA, Sigma Chemical Co., St. Louis, Missouri), at least 20 days prior to aerosol challenge by receiving 0.5 ml of EA-AlOH$_3$ conjugate (33 μg EA/ml) intramuscularly in each hind leg.

On the test day, fasted, sensitized guinea pigs are divided into a control group (8 animals per group) and test groups of four animals per group by using random number tables generated by an IBM scrambler. The reference; e.g., theophylline or test drug (Formula I cpd.) dissolved or suspended in 0.5% Tween 80 in distilled water or the control article (0.5% Tween 80 in distilled water) are administered orally in a volume of liquid at 10 ml/kg. Either 1, 5, or 24 hours following the oral administration of the test drug, reference drug, or control article, each animal is placed in an aerosolization chamber. EA (10 mg/ml) aerosolized at a rate of 10 liters of air/min is delivered into the chamber for a maximum of 5 minutes. The anaphylactic response consists of coughing, dyspnea, reeling, collapse and death. Upon collapsing, the animals are removed from the chamber. Animals are considered protected if they do not collapse within 5 min of exposure to the aerosolized antigen. The number of animals that collapse in each group is recorded. ED$_{50}$ for collapse is calculated by the method of Litchfield and Wilcoxon (1949), J. PHARMACOL. EXP. THERAP. 95, 99–113 for evaluation of dose-effect experiments. Comparisons of ED$_{50}$s from different experimental trials and determinations of relative potency are determined by the Litchfield and Wilcoxon method, ibid. The following conditions must be met before an experiment is acceptable:

(1) Control group shows collapse in 7/8 or 8/8 animals, and (2) Theophylline reference group shows protection in ¾ or 4/4 animals treated 1 hr or 5 hr prior to antigen exposure.

Pharmaceutical Compositions and Administration

Compositions for administration to living animals are comprised of at least one of the compounds of Formula I according to the antiallergy method of the invention in association with a pharmaceutical carrier or excipient. Effective quantitites of the compounds may be administered in any one of various ways, for example, orally as in elixirs, capsules, tablets or coated tablets, parenterally in the form of sterile solutions, suspensions, and in some cases intravenously in the form of sterile solutions, intranasally and to the throat or bronchial region in the form of drops, gargles, sprays, aerosols and powders, etc. or cutaneously as topical ointments, solutions, powders, etc. Suitable tableting excipients include lactose, potato and maize starches, talc, gelatin, stearic and silica acids, magnesium stearate and polyvinyl pyrrolidone.

For parenteral administration, the carrier or excipient can be comprised of a sterile parenterally acceptable liquid; e.g., water or arachis oil contained in ampoules.

Advantageously, the compositions are formulated as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the disage form employed, in multiples if necessary. The exact individual dosages, as well as daily dosages, will of course be determined according to standard medical principles under the direction of a physician or veterinarian. Generally, the pharmacology tests on guinea pigs in comparison to certain other anti-allergy drugs suggest an effective dose for an adult will be in the range of 1.0 to 20 mg for the more active compounds with a daily dosage amounting to about 4 to 160 mg/day.

Based on the animal data, unit dosages containing an amount of compound equivalent to about 0.02 to 0.2 mg of active drug per kilogram of body weight are contemplated. Daily dosages of about 0.10 to 2.0 mg/kg of body weight are contemplated for humans and obviously several small dosage forms may be administered at one time. However, the amount of the active compounds administered need not be limited by these contemplations due to uncertainty in transposing animal data to human treatment.

Examples of compositions within the preferred ranges given are as follows:

| Capsules | |
|---|---|
| Ingredients | Per Cap. |
| 1. Active ingredient | 10.00 mg |
| 2. Lactose | 146.000 mg |
| 3. Magnesium Stearate | 4.000 mg |

Procedure
1. Blend 1, 2 and 3.
2. Mill this blend and blend again.
3. This milled blend is then filled into #1 hard gelatin capsules.

| Tablets | |
|---|---|
| Ingredients | Mg./Tab. |
| 1. Active ingredient | 10.0 mg |
| 2. Corn Starch | 20.0 mg |
| 3. Alginic acid | 20.0 mg |
| 4. Sodium alginate | 20.0 mg |
| 5. Magnesium Stearate | 1.3 mg |

Procedure
1. Blend 1, 2, 3 and 4.
2. Add sufficient water portionwise to the blend from step #1 with careful stirring after each addition. Such additions of water and stirring continue until the mass is of consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
|---|---|
| Ingredients | Per ml. |
| 1. Active ingredient | 1.0 mg |
| 2. pH 4.0 Buffer solution | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | |
|---|---|
| Ingredients | Per ml |
| 1. Active ingredient | 5.0 mg |
| 2. Isotonic Buffer solution 4.0 | q.s. to 1.0 ml |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | |
|---|---|
| Ingredients | Per Supp. |
| 1. Active ingredient | 10.0 mg |
| 2. Polyethylene Glycol 1000 | 1350.0 mg |
| 3. Polyethylene Glycol 4000 | 450.0 mg |

Procedure
1. Melt 2 and 3 together and stir until uniform.
2. Dissolve #1 in the molten mass from step 1 and stir until uniform.
3. Pour the molten mass from step 2 into suppoository molds and chill.
4. Remove the suppositories from molds and wrap.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed is:
1. A compound selected from the group having the formula:

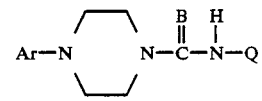

wherein;
B is oxygen or sulfur;
Ar is selected from

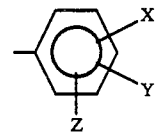

or 2, 3 or 4-pyridyl;
X is selected from hydrogen,
halogen,
loweralkyl,
loweralkoxy,
amino,
dimethylamino,
nitro,
trifluoromethyl,
cyano, acetyl,
acetylamino,
aminocarbonyl,
carboxy, or loweralkyl carboxylic acid ester;
Y is selected from hydrogen,
halogen,
loweralkyl,
loweralkoxy,
nitro,
trifluoromethyl,
cyano,
acetyl,
acetylamino,
aminocarbonyl,
carboxy, or loweralkyl carboxylic acid ester;
Z is selected from
hydrogen,
loweralkyl, or
loweralkoxy;
Q is selected from

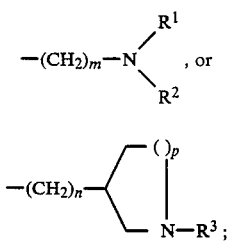

m is 1 to 3 inclusive;
n is zero or 1;
p is zero to 3 inclusive;
$R^1$, $R^2$ and $R^3$ are loweralkyl and may be the same or different, or $R^1$ and $R^2$ taken together with the adjacent nitrogen atom may form a heterocyclic residue, and the pharmaceutically acceptable salts thereof.

2. The compound of claim 1 which is 4-(3-chlorophenyl)-N-[2-(dimethylamino)ethyl]-1-piperazinecarboxamide or a pharmaceutically acceptable salt thereof.

3. The compound of claim 1 which is 4-(3-chlorophenyl)-N-[2-(diethylamino)ethyl]-1-piperazinecarboxamide or a pharmaceutically acceptable salt thereof.

4. The compound of claim 1 which is N-[2-(diethylamino)ethyl]-4-phenyl-1-piperazinecarboxamide or a pharmaceutically acceptable salt thereof.

5. The compound of claim 1 which is N-[3-(dimethylamino)propyl]-4-phenyl-1-piperazinecarboxamide or a pharmaceutically acceptable salt thereof.

6. The compound of claim 1 which is 4-phenyl-N-[2-(1-pyrrolidinyl)ethyl]-1-piperazinecarboxamide or a pharmaceutically acceptable salt thereof.

7. The compound of claim 1 which is 4-phenyl-N-[2-(1-piperidinyl)ethyl]-1-piperazinecarboxamide or a pharmaceutically acceptable salt thereof.

8. The compound of claim 1 which is N-[2-(dimethylamino)ethyl]-4-phenyl-1-piperazinecarboxamide or a pharmaceutically acceptable salt thereof.

9. The compound of claim 1 which is N-[2-(hexahydro-1H-azepin-1-yl)ethyl]-4-phenyl-1-piperazinecarboxamide or a pharmaceutically acceptable salt thereof.

10. The compound of claim 1 which is N-[2-(diethylamino)ethyl]-4-(2-pyridinyl)-1-piperazinecarboxamide or a pharmaceutically acceptable salt thereof.

11. The compound of claim 1 which is N-[2-(dimethylamino)ethyl]-4-(4-fluorophenyl)-1-piperazinecarboxamide or a pharmaceutically acceptable salt thereof.

12. The compound of claim 1 which is N-[2-(diethylamino)ethyl]-4-(4-fluorophenyl)-1-piperazinecarboxamide or a pharmaceutically acceptable salt thereof.

13. The compound of claim 1 which is 4-(2-chlorophenyl)-N-[2-(dimethylamino)ethyl]-1-piperazinecarboxamide or a pharmaceutically acceptable salt thereof.

14. The compound of claim 1 which is 4-(4-chlorophenyl)-N-[2-(dimethylamino)ethyl]-1-piperazinecarboxamide.

15. The compound of claim 1 which is N-[2-(dimethylamino)ethyl]-4-(2-pyridinyl)-1-piperazinecarboxamide or a pharmaceutically acceptable salt thereof.

16. The compound of claim 1 which is N-[2-(dimethylamino)ethyl]-4-(4-methoxyphenyl)-1-piperazinecarboxamide or a pharmaceutically acceptable salt thereof.

17. The compound of claim 1 which is N-[2-(dimethylamino)ethyl]-4-(3-methoxyphenyl)-1-piperazinecarboxamide or a pharmaceutically acceptable salt thereof.

18. The compound of claim 1 which is N-[2-(dimethylamino)ethyl]-4-(3,4,5-trimethoxyphenyl)-1-piperazinecarboxamide or a pharmaceutically acceptable salt thereof.

19. The compound of claim 1 which is 4-(3,4-dichlorophenyl)-N-[2-(dimethylamino)ethyl]-1-piperazinecarboxamide or a pharmaceutically acceptable salt thereof.

20. The compound of claim 1 which is N-[2-(dimethylamino)ethyl]-4-[3-(trifluoromethyl)phenyl]-1-piperazinecarboxamide or a pharmaceutically acceptable salt thereof.

21. The compound of claim 1 which is N-[2-(dimethylamino)ethyl]-4-(4-methylphenyl)-1-piperazinecarboxamide or a pharmaceutically acceptable salt thereof.

22. The compound of claim 1 which is 4-(3,4-dimethoxyphenyl)-N-[2-(dimethylamino)ethyl]-1-piperazinecarboxamide or a pharmaceutically acceptable salt thereof.

23. The compound of claim 1 which is N-[2-(dimethylamino)ethyl]-4-(2-methoxyphenyl)-1-piperazinecarboxamide or a pharmaceutically acceptable salt thereof.

24. The compound of claim 1 which is N-[2-(dimethylamino)ethyl]-4-(4-nitrophenyl)-1-piperazinecarboxamide or a pharmaceutically acceptable salt thereof.

25. The compound of claim 1 which is N-[2-(dimethylamino)ethyl]-4-[4-(dimethylamino)phenyl]-1-piperazinecarboxamide or a pharmaceutically acceptable salt thereof.

26. The compound of claim 1 which is N-[2-(dimethylamino)ethyl]-4-(3-fluorophenyl)-1-piperazinecarboxamide or a pharmaceutically acceptable salt thereof.

27. The compound of claim 1 which is N-[2-(dimethylamino)ethyl]-4-(2-fluorophenyl)-1-piperazinecarboxamide or a pharmaceutically acceptable salt thereof.

28. The compound of claim 1 which is 4-(4-fluorophenyl)-N-[2-(pyrrolidinyl)ethyl]-1-piperazinecarboxamide or a pharmaceutically acceptable salt thereof.

29. The compound of claim 1 which is 4-(4-cyanophenyl)-N-[2-(dimethylamino)ethyl]-1-piperazinecarboxamide or a pharmaceutically acceptable salt thereof.

30. The compound of claim 1 which is 4-(4-bromophenyl)-N-[2-(dimethylamino)ethyl]-1-piperazinecarboxamide or a pharmaceutically acceptable salt thereof.

31. The compound of claim 1 which is 4-(4-aminophenyl)-N-[2-(dimethylamino)ethyl]-1-piperazinecarboxamide or a pharmaceutically acceptable salt thereof.

32. The compound of claim 1 which is 4-(4-acetylphenyl)-N-[2-(dimethylamino)ethyl]-1-piperazinecarboxamide or a pharmaceutically acceptable salt thereof.

33. The compound of claim 1 which is 4-[4-(aminocarbonyl)phenyl]-N-[2-(dimethylamino)ethyl]-1-piperazinecarboxamide or a pharmaceutically acceptable salt thereof.

34. The compound of claim 1 which is 4-[4-[[[2-dimethylamino)ethyl]amino]carbonyl]-1-piperazinyl]benzoic acid ethyl ester or a pharmaceutically acceptable salt thereof.

35. The compound of claim 1 which is 4-[4-(acetylamino)phenyl]-N-[2-(dimethylamino)ethyl]-1-piperazinecarboxamide or a pharmaceutically acceptable salt thereof.

36. The compound of claim 1 which is N-(1-ethyl-3-piperidinyl)-4-phenyl-1-piperazinecarboxamide or a pharmaceutically acceptable salt thereof.

37. A method of inhibiting Type I allergic response in a living animal body which comprises administering to said animal in need thereof a compound selected from the group having the formula:

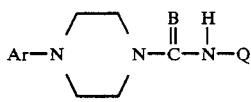

wherein;
B is oxygen or sulfur;
Ar is selected from

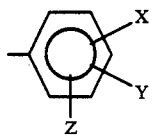

or 2, 3 or 4-pyridyl;
X is selected from hydrogen,
halogen,
loweralkyl,
loweralkoxy,
amino,
dimethylamino,
nitro,
trifluoromethyl,
cyano,
acetyl,
acetylamino,
aminocarbonyl,
carboxy, or
loweralkyl carboxylic acid ester;
Y is selected from hydrogen,
halogen,
loweralkyl,
loweralkoxy,
nitro,
trifluoromethyl,
cyano,
acetyl,
acetylamino,
aminocarbonyl,
carboxy, or
loweralkyl carboxylic acid ester;
Z is selected from
hydrogen,
loweralkyl, or
loweralkoxy;
Q is selected from

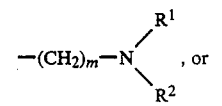

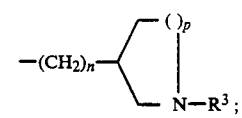

m is 1 to 3 inclusive;
n is zero or 1;
p is zero to 3 inclusive;
$R^1$, $R^2$ and $R^3$ are loweralkyl and may be the same or different, or $R^1$ and $R^2$ taken together with the adjacent nitrogen atom may form a heterocyclic residue, and the pharmaceutically acceptable salts thereof.

38. The method of claim 37 wherein the compound used is 4-(3-chlorophenyl)-N-[2-(dimethylamino)ethyl]-1-piperazinecarboxamide or a pharmaceutically acceptable salt thereof.

39. The method of claim 37 wherein the compound used is 4-(3-chlorophenyl)-N-[2-(diethylamino)ethyl]-1-piperazinecarboxamide or a pharmaceutically acceptable salt thereof.

40. The method of claim 37 wherein the compound used is N-[2-(diethylamino)ethyl]-4-phenyl-1-piperazine-carboxamide or a pharmaceutically acceptable salt thereof.

41. The method of claim 37 wherein the compound used is N-[3-(dimethylamino)propyl]-4-phenyl-1-piperazinecarboxamide or a pharmaceutically acceptable salt thereof.

42. The method of claim 37 wherein the compound used is 4-phenyl-N-[2-(1-pyrrolidinyl)ethyl]-1-piperazine-carboxamide or a pharmaceutically acceptable salt thereof.

43. The method of claim 37 wherein the compound used is 4-phenyl-N-[2-(1-piperidinyl)ethyl]-1-piperazine-carboxamide or a pharmaceutically acceptable salt thereof.

44. The method of claim 37 wherein the compound used is N-[2-(dimethylamino)ethyl]-4-phenyl-1-piperazine-carboxamide or a pharmaceutically acceptable salt thereof.

45. The method of claim 37 wherein the compound used is N-[2-(hexahydro-1H-azepin-1-yl)ethyl]-4-phenyl-1-piperazinecarboxamide or a pharmaceutically acceptable salt thereof.

46. The method of claim 37 wherein the compound used is N-[2-(diethylamino)ethyl]-4-(2-pyridinyl)-1-piperazine-carboxamide or a pharmaceutically acceptable salt thereof.

47. The method of claim 37 wherein the compound used is N-[2-(dimethylamino)ethyl]-4-(4-fluorophenyl)-1-piperazinecarboxamide or a pharmaceutically acceptable salt thereof.

48. The method of claim 37 wherein the compound used is N-[2-(diethylamino)ethyl]-4-(4-fluorophenyl)-1-piperazinecarboxamide or a pharmaceutically acceptable salt thereof.

49. The method of claim 37 wherein the compound used is 4-(2-chlorophenyl)-N-[2-(dimethylamino)ethyl]-1-piperazinecarboxamide or a pharmaceutically acceptable salt thereof.

50. The method of claim 37 wherein the compound used is 4-(4-chlorophenyl)-N-[2-(dimethylamino)ethyl]-1-piperazinecarboxamide or a pharmaceutically acceptable salt thereof.

51. The method of claim 37 wherein the compound used is N-[2-(dimethylamino)ethyl]-4-(2-pyridinyl)-1-piperazinecarboxamide or a pharmaceutically acceptable salt thereof.

52. The method of claim 37 wherein the compound used is N-[2-(dimethylamino)ethyl]-4-(4-methoxyphenyl)-1-piperazinecarboxamide or a pharmaceutically acceptable salt thereof.

53. The method of claim 37 wherein the compound used is N-[2-(dimethylamino)ethyl]-4-(3-methoxyphenyl)-1-piperazinecarboxamide or a pharmaceutically acceptable salt thereof.

54. The method of claim 37 wherein the compound used is N-[2-(dimethylamino)ethyl]-4-(3,4,5-trimethoxyphenyl)-1-piperazinecarboxamide or a pharmaceutically acceptable salt thereof.

55. The method of claim 37 wherein the compound used is 4-(3,4-dichlorophenyl)-N-[2-(dimethylamino)ethyl]-1-piperazinecarboxamide or a pharmaceutically acceptable salt thereof.

56. The method of claim 37 wherein the compound used is N-[2-(dimethylamino)ethyl]-4-[3-(trifluoromethyl)phenyl]-piperazinecarboxamide or a pharmaceutically acceptable salt thereof.

57. The method of claim 37 wherein the compound used is N-[2-(dimethylamino)ethyl]-4-(4-methylphenyl)-1-piperazinecarboxamide or a pharmaceutically acceptable salt thereof.

58. The method of claim 37 wherein the compound used is 4-(3,4-dimethoxyphenyl)-N-[2-(dimethylamino)ethyl]-1-piperazinecarboxamide or a pharmaceutically acceptable salt thereof.

59. The method of claim 37 wherein the compound used is N-[2-(dimethylamino)ethyl]-4-(2-methoxyphenyl)-1-piperazinecarboxamide or a pharmaceutically acceptable salt thereof.

60. The method of claim 37 wherein the compound used is N-[2-(dimethylamino)ethyl]-4-(4-nitrophenyl)-1-piperazinecarboxamide or a pharmaceutically acceptable salt thereof.

61. The method of claim 37 wherein the compound used is N-[2-(dimethylamino)ethyl]-4-[4-(dimethylamino)phenyl-1-piperazinecarboxamide or a pharmaceutically acceptable salt thereof.

62. The method of claim 37 wherein the compound used is N-[2-(dimethylamino)ethyl]-4-(3-fluorophenyl)-1-piperazinecarboxamide or a pharmaceutically acceptable salt thereof.

63. The method of claim 37 wherein the compound used is N-[2-(dimethylaminp)ethyl]-4-(2-fluorophenyl)-1-piperazinecarboxamide or a pharmaceutically acceptable salt thereof.

64. The method of claim 37 wherein the compound used is 4-(4-fluorophenyl)-N-[2-(1-pyrrolidinyl)ethyl]-1-piperazinecarboxamide or a pharmaceutically acceptable salt thereof.

65. The method of claim 37 wherein the compound used is 4-(4-cyanophenyl)-N-[2-(dimethylamino)ethyl]-1-piperazinecarboxamide or a pharmaceutically acceptable salt thereof.

66. The method of claim 37 wherein the compound used is 4-(4-bromophenyl)-N-[2-(dimethylamino)ethyl]-1-piperazinecarboxamide or a pharmaceutically acceptable salt thereof.

67. The method of claim 37 wherein the compound used is 4-(4-aminophenyl)-N-[2-(dimethylamino)ethyl]-1-piperazinecarboxamide or a pharmaceutically acceptable salt thereof.

68. The method of claim 37 wherein the compound used is 4-(4-acetylphenyl)-N-[2-(dimethylamino)ethyl]-1-piperazinecarboxamide or a pharmaceutically acceptable salt thereof.

69. The method of claim 37 wherein the compound used is 4-[4-(aminocarbonyl)phenyl]-N-[2-(dimethylamino)ethyl]-1-piperazinecarboxamide or a pharmaceutically acceptable salt thereof.

70. The method of claim 37 wherein the compound used is 4-[4-[[[2-(dimethylamino)ethyl]amino]carbonyl]-1-piperazinyl]benzoic acid ethyl ester or a pharmaceutically acceptable salt thereof.

71. The method of claim 37 wherein the compound used is 4-[4-(acetylamino)phenyl]-N-(2-(dimethylamino)ethyl]-1-piperazinecarboxamide or a pharmaceutically acceptable salt thereof.

72. The method of claim 37 wherein the compound used is N-(1-ethyl-3-piperidinyl)-4-phenyl-1-piperazinecarboxamide or a pharmaceutically acceptable salt thereof.

73. A pharmaceutical composition for combating allergy in unit dosage form comprising (a) an effective amount of a compound selected from those having the formula:

$$Ar-N\diagup\diagdown N-\overset{B}{\overset{\|}{C}}-\overset{H}{\overset{|}{N}}-Q$$

wherein;
B is oxygen or sulfur;
Ar is selected from phenyl,

[structure: phenyl ring with substituents X, Y, Z]

or 2, 3 or 4-pyridyl;
X is selected from hydrogen,
  halogen,
  loweralkyl,
  loweralkoxy,
  amino,
  dimethylamino,
  nitro,
  trifluoromethyl,
  cyano,
  acetyl,
  acetylamino,
  aminocarbonyl,
  carboxy, or
  loweralkyl carboxylic acid ester;
Y is selected from
  hydrogen,
  halogen, loweralkyl,
loweralkoxy,
nitro,
trifluoromethyl,
cyano,
acetyl,
acetylamino,
aminocarbonyl,
carboxy, or
loweralkyl carboxylic acid ester;
Z is selected from
hydrogen,
loweralkyl, or
loweralkoxy;
Q is selected from

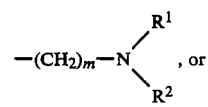

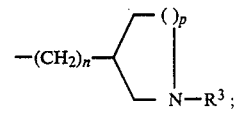

m is 1 to 3 inclusive;
n is zero or 1;
P is zero to 3 inclusive;
$R^1$, $R^2$ and $R^3$ are loweralkyl and may be the same or different, or $R^1$ and $R^2$ taken together with the adjacent nitrogen atom may form a heterocyclic residue, and the pharmaceutically acceptable salts thereof.
and, (b) a suitable pharmaceutical carrier therefor.

* * * * *